United States Patent [19]

Eaton

[11] Patent Number: 5,531,103

[45] Date of Patent: Jul. 2, 1996

[54] METHOD AND APPARATUS FOR DETERMINING VELOCITY DEPENDENT CORROSION RATE

[75] Inventor: Paul Eaton, Houston, Tex.

[73] Assignee: Champion Technologies, Inc., Fresno, Tex.

[21] Appl. No.: 376,768

[22] Filed: Jan. 23, 1995

[51] Int. Cl.⁶ ................................................. G01N 33/18
[52] U.S. Cl. ........................................ 73/61.62; 73/61.63
[58] Field of Search .................................. 73/198, 61.62, 73/61.41, 61.46, 61.47, 61.48, 61.49, 61.63, 61.67, 61.71; 324/700; 422/53

[56] References Cited

U.S. PATENT DOCUMENTS

| | | | |
|---|---|---|---|
| 3,392,575 | 7/1968 | Galler | 73/62.62 |
| 4,176,544 | 12/1979 | Eyles et al. | 73/61.62 |
| 4,383,438 | 5/1983 | Eaton | 73/61.62 |
| 4,654,187 | 3/1987 | Feges et al. | 73/61.62 |
| 5,068,196 | 11/1991 | Hays et al. | 73/61.62 |
| 5,361,284 | 11/1994 | Baum et al. | 422/53 |

*Primary Examiner*—Richard Chilcot
*Assistant Examiner*—Max Noori
*Attorney, Agent, or Firm*—Gunn & Associates

[57] ABSTRACT

In testing for pipeline corrosion, a test loop is provided. The loop has three parallel legs, each having a corrosion test cell. The three parallel legs provide flow at different velocities. Corrosion inhibitor is injected and data is collected from the test cells so that the correlation between fluid flow temperature, pressure and valocity of the fluid flow.

17 Claims, 2 Drawing Sheets

METHOD AND APPARATUS FOR DETERMINING VELOCITY DEPENDENT CORROSION RATE

BACKGROUND OF THE INVENTION

This disclosure is directed to a method and apparatus useful in determining the rate of corrosion. Corrosion occurs in pipelines made of metal. The corrosion which occurs is a function of many factors. In an effort to counteract the rate of corrosion, corrosion inhibitors are injected into the flowing material in the pipeline. It is important to get the right amount of inhibitor material in the pipeline. If insufficient material is injected, inadequate protection will be achieved and corrosion may nevertheless still occur. By contrast, if excessive corrosion inhibitor material is injected, it may be wasted, and it is usually an expensive additive. For these reasons, it is desirable to determine the right rate at which the injection material is injected. This particular situation has a long protective term aspect which enables the metal forming the pipeline to be protected and to extend the life of the pipeline. The rate of corrosion and hence the severity of corrosion increases with a number of factors. However, these increases are not necessarily linear.

It is intended that a corrosion inhibitor be injected at a required volume taking into account the flow rate so that the corrosion of metal can be substantially reduced. The inhibitors which are added significantly interact with the wall of the pipeline. At the wall, there may well be a "coated" metal surface. The surface is normally coated by reaction products which are obtained from partial corrosion, that is, intermediates of the corrosion process. Sometimes, the corrosion process is relatively complicated and forms numerous intermediates. Take as an example a simple situation, namely, one in which a flowing liquid product includes water and is flowing in a steel pipeline. The water will react with the wall of the pipe and form rust meaning various oxides of the iron in the steel pipe. This will form a highly undesirable rust layer. Clearly, the thickness of the layer will vary and the precise mix of the oxides of iron will likewise vary. Intermediates may be formed which are different types of iron oxide. Furthermore, the layer construction may vary i.e., it may be open or porous so that other products can penetrate through the surface material and still react with the metal layer beneath the corrosion layer. Corrosion layers typically are accumulated to the detriment of the pipeline. In many instances, it may be important to achieve an impervious layer on the wall of the pipe. The inhibitor is added to the flowing pipeline product so that the inhibitor product reacts with the flowing product and the surrounding pipeline to thereby form a coating which inhibits further chemical reaction with the metal forming the pipeline. It is especially important to screen the steel of the pipeline from sulfur related products and especially H2S. H2S has a propensity for severe damage to a pipeline. In one aspect of the present invention, coating is assumed to be formed on the interior of the pipeline, and with regard to the coating, the present system enables measurements to be made.

The rate of corrosion depends on very complex factors. It is highly desirable to know the rate of corrosion so that protective steps can be taken. In one aspect of the present invention, a flow loop is set forth which utilizes a closed loop having a high pressure pump connected in the loop to thereby provide fluid flow at a specified velocity. It has been learned that the rate of corrosion is dependent on several significant factors, and others may be applicable in other circumstances. One important factor is the temperature of the flowing material. While the product may be substantially inert, as the temperature is increased, it becomes a more reactive material in ordinary circumstances. The rate of corrosion is also dependent on the velocity of the flowing liquid. Fluid traveling at an elevated velocity changes the manner or mode in which the flowing fluid reacts with the wall of the pipe. The inhibitor may be flushed away from the wall of the pipe. When this occurs, substantial protection which would otherwise be present at low velocities is lost and may not be available at high velocities.

Not only do temperature and velocity have an impact on the flow rate, but the corrosion rate is also dependent on ambient pressure. In other words, for a given set of circumstances, if the pressure were increased by 100%, the corrosion rate is changed as a result of that interaction.

As will be understood, the examples of pressure, temperature and velocity are simply three of the several variables which interact to describe the corrosion rate. Even more profoundly, the corrosion rate still must be evaluated with respect to other factors. Suffice it to say, the rate of corrosion is a relatively complex relationship and is dependent on the three mentioned factors and also on other factors and can be generally described as a nonlinear relationship.

The present disclosure is directed to a method and apparatus for determining the flow rate of corrosion. More particularly, the present disclosure sets forth a system which includes a test loop for providing controlled fluid flow where the above mentioned three physical factors can be varied. That is, the system is able to vary pressure, flow rate, and temperature. In this aspect, the test loop utilizes suitable storage tanks which furnish the necessary test fluid. As desired, a gas drive can be applied behind the system to assure that the pressure is brought up to the requisite test range. Coupled with this, the system also contemplates the use of multiple lines cooperative with individual test cells to obtain different corrosion rates for differing flow rates. More specifically, multiple test cells are arranged and deployed in conjunction with test instrumental which provides needed measurements. The corrosion cell utilizes metal coupons which are exposed to the fluid flow. The metal coupons in the preferred embodiment are brought into contact with the flowing liquid. In particular, the flowing liquid is exposed so that the surface is necessarily impacted by the corrosion inhibitors when added to the fluid flow, and a corrosion rate is determined from that. Utilizing a potentiostat, the rate of corrosion on these steel coupons can be determined. In addition to that, the rate of corrosion is also measured through the use of a variable frequency oscillator (VFO) to provide a sweep frequency signal. This is done in conjunction with a pair of test coupons to provide an indication of the nature of the corrosion, and which is subject to later interpretation to provide some indication of the rate of corrosion buildup, the rate of protection, and the ability of the corrosion inhibitor to prevail notwithstanding extraordinary high pressure, flow velocities, and temperatures. Other variables may be adjusted also and data regarding them is obtained so that the indications of the corrosion rate can be correlated to any number of variable factors. As an example, one variable factor is the presence of $H_2S$ in the flowing liquid which has its own particular impact on the corrosion rate.

BRIEF SUMMARY OF THE PRESENT DISCLOSURE

This system is a flow loop which is constructed for testing the rate of corrosion in a corrosion test cell. In one version of the flow loop, a pump is connected to deliver a flowing liquid at a specified pressure. A tank of liquid stores liquid in a heater so that a specified temperature can be achieved for the liquid. The materials for the simulated liquid are provided from two alternate tanks which are mixed in a specified ratio to assure that the test liquid is formed of the proper constituents. Furthermore, the test loop includes a flowmeter. Duplicate legs in the test loop each include a separate cell. By control of dimensions, the flow rate through the multiple legs and hence through the multiple test cells is controlled. In other words, a specified velocity can be achieved in each of the test cells and the velocities can be similar or different. Each test cell is formed of circular steel coupons which have a central hole thereby forming a portion of the sidewall which is exposed to the flowing liquid. More importantly, the flowing liquid acts against the coupons to form corrosion products. Any corrosion inhibitor that is added to the flowing liquid reacts with the coupon to controllably retard corrosion. Through the use of test circuitry connected to the coupons, selected measurements can be obtained. The several measurements include a test of DC current flow from one to the next coupon. Another test involves sweeping the test cell with a VFO to measure the frequency dependency of the test cell in a particular set of conditions. Accordingly, control of pressure, velocity, and temperature along with other variable can be achieved in the test period.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
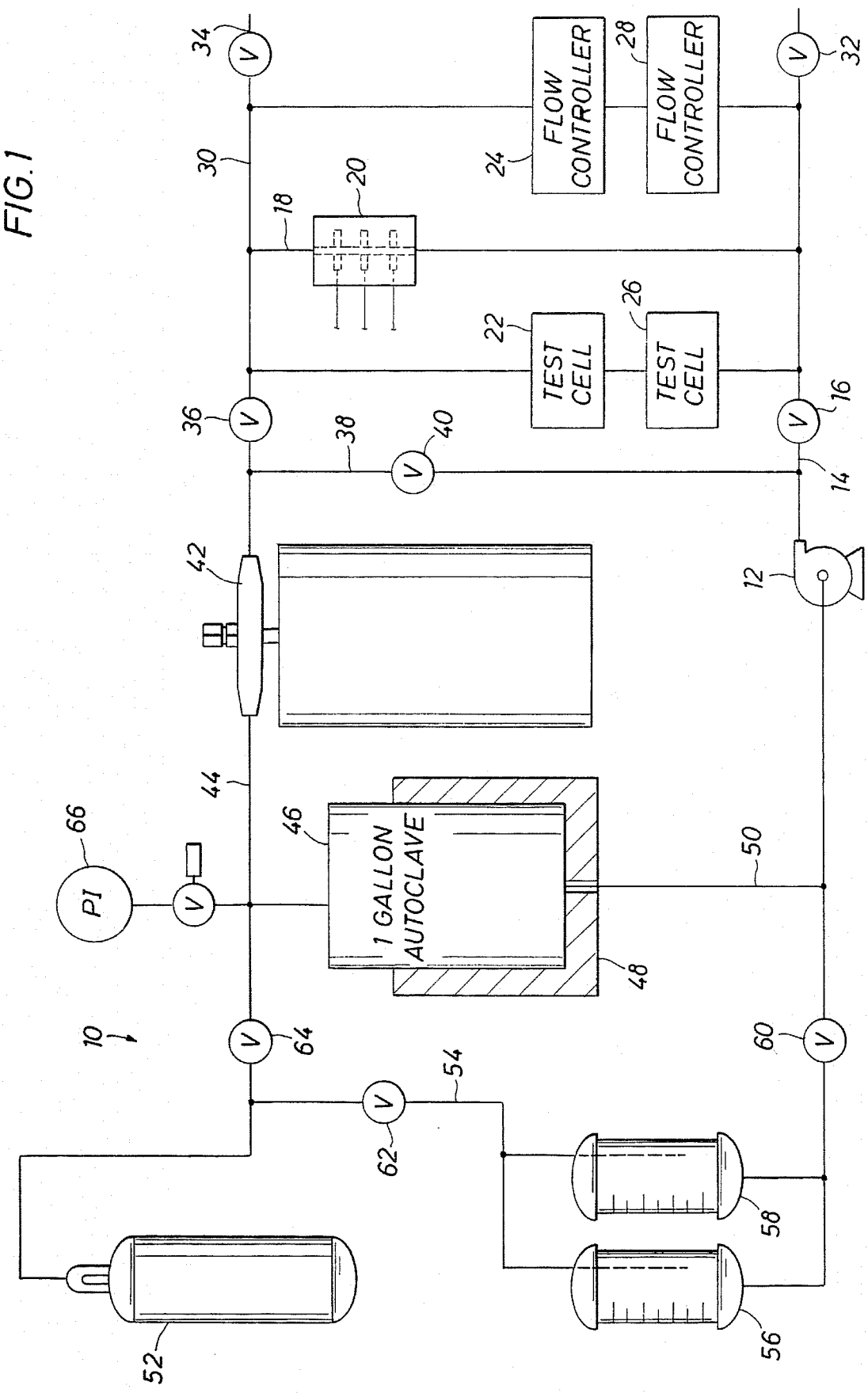
FIG. 1 is a flow path of a test loop showing piping and connections to provide fluid flow through one or more corrosion test cells connected in one or more parallel legs of the test loop.

Attention is first directed to FIG. 1 of the drawings in which the numeral 10 identifies a test loop. This test loop is constructed and arranged to provide for testing of a flowing liquid and more particularly a liquid which can be mixed from multiple components. It is used in testing for corrosion inhibitors. Describing first the test loop, the numeral 12 identifies a high pressure pump which delivers high pressure liquid flow out of the pump 12 through a supply line 14. The supply line is connected to a valve 16 which enables the test to be initiated. The valve 16 provides the flowing liquid at a required pressure and temperature to three duplicate legs which go through three duplicate test cells. More particularly, the line 18 connects with a test cell 20 which is duplicated in all aspects by similar test cells 22 and 24. The cells 20, 22 and 24 are connected in identical flow lines. They deliver the same flowing liquid at a common temperature. They differ only in that the test cells 22 and 24 are connected downstream of flow controllers 26 and 28. For instance, the controllers can readily be a restriction in the flow line such as an orifice or the like. Suffice it to say, the three test cells are identical in construction and operation. They are also identical in the mode of operation while they differ only in that the flow through the three test cells is different. The velocity through the three test cells is varied because that is a significant factor. As an example, the velocity through one line can be one foot per second, the second line 10 feet per second and third test cell velocity can be 50 feet per second. The lines which connect through the test cells all connect to a common header 30. Drain valves 32 and 34 are included for the supply line and header respectively. An isolation valve 36 is also included in the header as needed. If the occasion demands, a bypass line 38 is included so that no flow is directed through the test cells. This requires opening of the bypass valve 40.

The discharge liquid flow from the several lines is delivered through a mass flowmeter 42. The mass flowmeter is connected to a recirculation line 44 which is then is input to a tank 46 which is in an oven 48 which is heated by any suitable means (not illustrated). The output of the tank is delivered through a line 50 which is input to the pump 12 for recirculation.

Additional liquid can be added as desired. To this end, a high pressure cylinder of supply gas is included at 52. This is input to a sparge line 54. The sparge line is positioned in a test brine container 56 and a test oil container 58. In addition, the brine and test oil can be forced out of the respective tanks and through a supply valve 60 to flow into the pump 12. This enables simulated liquid to be added. The gas supply can be controlled by suitable isolation valves 62 and 64. The discharge pressure is measured by a pressure gauge 66. Other instrumentation including different pressure gauges and thermometers are installed at suitable locations.

Figure 2:
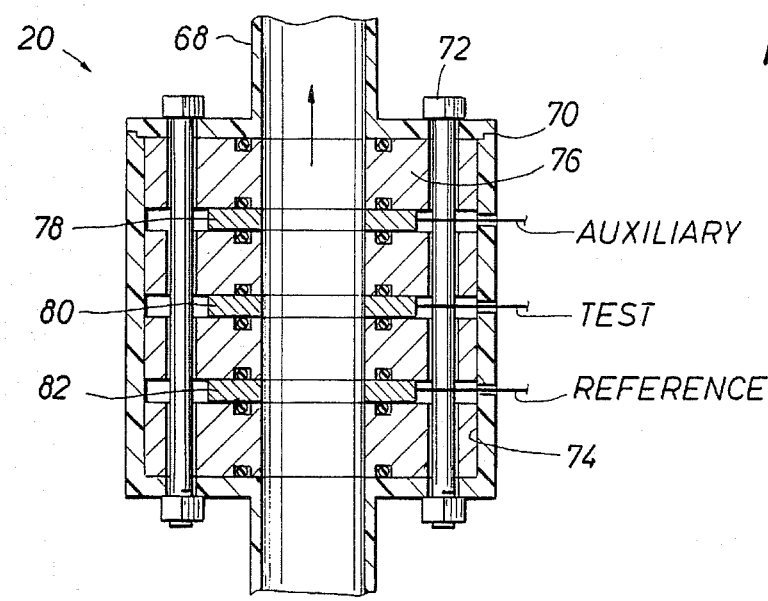
FIG. 2 is a sectional view through an electrochemical corrosion cell incorporating test coupons which are exposed to the flowing liquid.

Attention is now directed to FIG. 2 of the drawings which shows one of the test cells. Here, the cell 20 is shown in sectional view, it being noted that the pipe 68 connects into the shell 70. The shell 70 is assembled with axial loading by a set of head bolts 72 which connect to suitable nuts at the opposite end. Their purpose will be detailed momentarily. An internal liner 74 is included to provide electrical isolation to prevent shorting of the components. This internal lining 74 can be a rubber sleeve or an anodized surface, or the like. The numeral 76 identifies a spacer which is inserted between the ends of the cylindrical container 70. The spacer 76 is included for that purpose. It is perforated with suitable opening so that several head bolts 72 can pass through the spacer 76. The spacer is immediately adjacent to a circular steel coupon 78 which is inserted so that it has an inside diameter (id.) which is identical with the pipeline 68. Similar coupons 80 and 82 are likewise included. The three coupons are isolated by four insulative spacers 76. This provides electrical isolation of all three of the coupons. They are clamped snugly so no leakage occurs between the individual coupons and the spacer plates 76. To prevent leakage, suitable seals rings are located in appropriate grooves around the central passage through the test cell 20. After the equipment is fully assembled and the bolts are pulled snug, liquid is pumped through the test cell in one direction, a representative direction being selected as indicated by the arrow so the fluid flow contacts the metal coupons 78, 80 and 82.

The test cell is electrically isolated in all aspects except that electrical connections are extended from the three coupons to connect with other components as will be described briefly. One important aspect of this construction is that the cylindrical hole in each coupon precisely matches the diameter of the pipe 68. The several spacers 76 align with the several coupons to form an axial bore made of many components arranged so that the structure is able to provide a uniform diameter. The uniform diameter refers to the hole size; the material presented to the flowing product is not uniform. The respectively identified coupons are electrically insulated so that are not in contact with the metal which makes up the plumbing system otherwise in the flow loop of FIG. 1.

Figure 3:
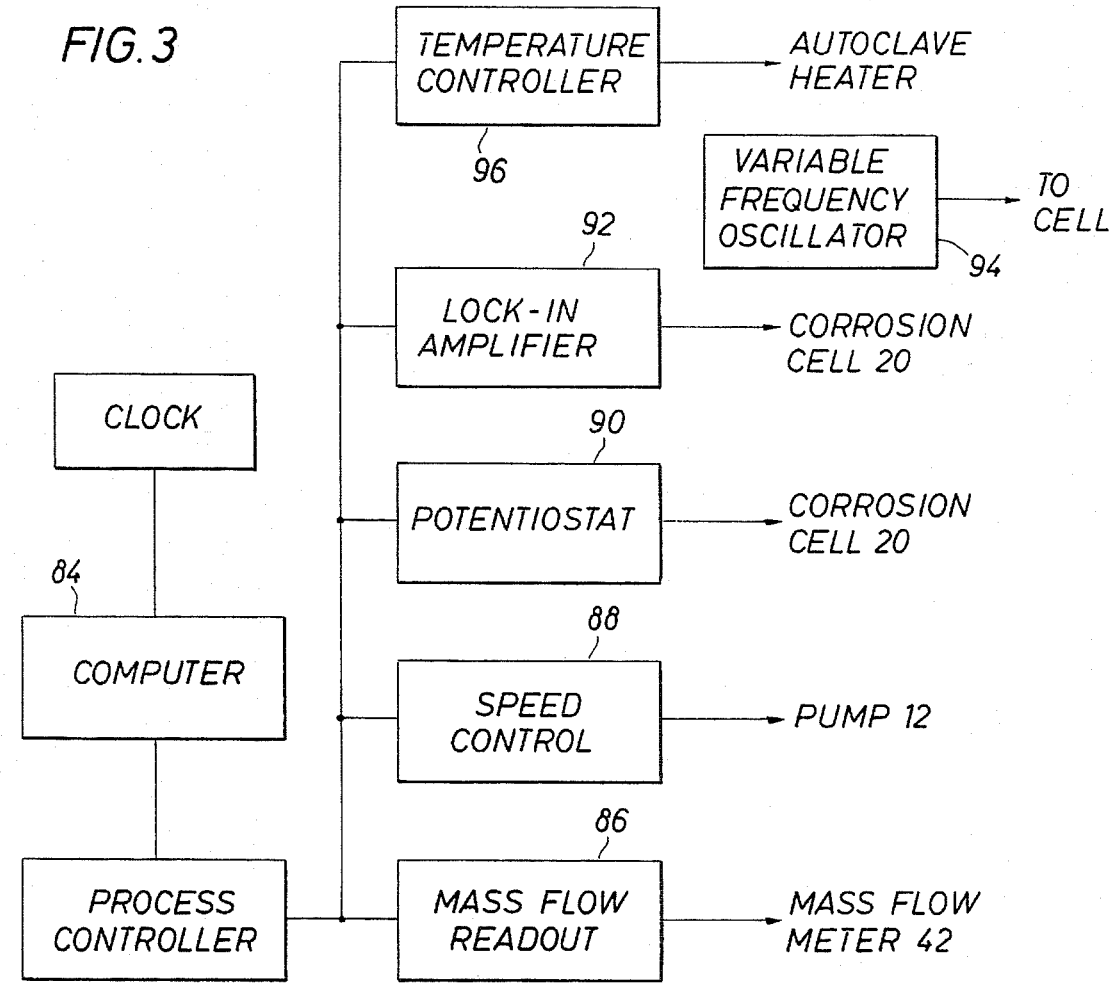
FIG. 3 is a schematic block diagram of a control system including test circuitry for use in determining the rate of corrosion.

Going now to FIG. 3 of the drawings, the test equipment is shown. The numeral 84 identifies a computer (CPU) having a memory with a process controller connected to it. This system includes a clock which enables the system to operate in a controlled and timed mode of operation.

Another important aspect of the equipment shown in FIG. 3 of the drawings is the availability of the system to capture and record data so that the data can be entered as a function of time and other variables. The system incorporates the mass flowmeter 42 previously mentioned and that works with a flowmeter device 86. In addition, there is a speed controller 88 for the pump 12. A potentiostat 90 is likewise included and it provides a measurement of the voltage between two of the coupons in the test cells.

One important component is the amplifier 92. That operates in conjunction with a VFO 94 to provide a frequency sweep signal across a test cell as will be detailed momentarily. The output of the test cell from the VFO sweep is meaningful data which is then provided to the computer 84 to be recorded. FIG. 3 also shows a temperature controller 96 which is connected with a heater (not shown) which warms the liquid in the tank 46.

Operation of the apparatus shown in FIG. 3 in conjunction with the cell of FIG. 2 should be considered. Consider any two coupons shown in FIG. 2 of the drawings. A circuit is completed through any two coupons based on the amount of corrosion deposited in the pipe 68. Adjacent coupons 80 and 82 are used in such an example. Assume for purposes of description that the coupon 82 serves as ground or a reference point. The coupon 80 is then the test point. The potential between the coupons 80 and 82 is measured by the potentiostat and that voltage is noted. That is significant to the corrosion process and measurement of the rate of corrosion. Restated, the rate of corrosion changes the voltage difference between the coupons 80 and 82. In addition to that, the VFO 94 is connected so that the variable frequency is input to a pair of coupons such as 80 and 82. When this occurs, the input signal is swept from some designated minimum to some designated maximum frequency. This sweep is performed over a specified interval of time. For instance, it is possible to sweep the signal from a very low frequency such as a fraction of hertz to some designated maximum frequency. The sweep frequency range can be several orders of magnitude as for example from 0.1 up to 100,000 hertz. The sweep frequency signal applied between the two electrodes is utilized to form an input to the electrode pair. The amplifier 92 is input to observe the output current level and cross coupon voltage level as a function of sweep frequency. This is recorded and will be used in conjunction with other data to analyze the nature of the corrosion process.

Perhaps an example will make this more clear. Consider as an example a first instance where corrosion inhibitors are tested for several different liquid conditions. In one example, assume that the liquid is heated to 200° F. Assume also that the system pressure is quite high, namely about 2000 psi. Assume also the velocity of the flowing liquid through the three cells is one foot per second, ten feet per second, and fifty feet per second. To provide such a test system, the components preferably are formed of specialty alloys such as Hasteloy (a trademark) or any alloy capable of resisting attack by $H_2S$ or various chloride solutions.

In a representative size, the system 10 shown in FIG. 1 of the drawings has a fluid capacity of about 5 liters. The corrosion coupons have an area of 15 centimeters square. This enables mounting flush with the interior of the pipe which has an id. of ⅞ inch.

One test procedure is to make a mixture of crude oil and salt water. One of the first steps is to store the brine and test oil in the containers 56 and 58. The gas source 52 is switched on by opening the appropriate valves 62 while closing the valve 64 to thereby introduce a sparging gas into the vessels 56 and 58. This is necessary to remove dissolved oxygen. Other liquids can be used such as a synthetic brine. The synthetic brine should be formulated so that it approximates field brine with regard to various constituents. In other words, the chlorides, sulfates and metal ions ought to be held equal to the typical flowing mixture within about 5%. The crude oil typical of the setting can be used. If not, an alternative that is acceptable is depolarized kerosene.

The liquid flow through the test loop is initiated through the control equipment shown in FIG. 3 of the drawings. Quite obviously, a specified pressure is implemented at a selected temperature is also input to the system. Mixing of the constituents is achieved from the tanks 56 and 58 after sparging. The ratio of the brine to the hydrocarbon should duplicate the production liquid that is otherwise input to the system.

One aspect of the present disclosure is a typical procedure which will be described below. This procedure is specific to a particular test. As will be understood, certain ratios are provided which are merely representative and can be varied. In this particular instance, assume that a particular brine solution is required and is made to provide a known content. It is stored in the water vessel 56. That is, the vessel 56 is filled with brine made to that specific set of salt requirements. Likewise, the requisite volume of oil is charged to the container 58. Assume for purpose of description that the brine constitutes 5% and the oil represents 95%. Assume further for purposes of example that the particular oil is a crude oil known as Amoco Ricinus. The goal in this test is to determine the effectiveness of selected separate corrosion inhibitors which are provided at concentrations of 10, 50 and 100 ppm. Specific inhibitors selected for this test included such specific products as RU-189, CRW-100A and T-8056.

Before any test, the system is purged and cleansed again. Again, the foregoing ratio of 5% brine and 95% crude was selected and that feed liquids were placed in the two containers 56 and 58 respectively. The gas in the cylinder 52 is preferably $N_2$. The valve 62 is opened to initiate sparge of the liquid in the containers 56 and 58 and sparging continues for at least six hours. A test cell utilizing new coupons was assembled and placed in the flow loop. The loop was then purged with a flow of carbon dioxide through the valve 64. Discharge from the loop uses either the dump valves 32 or 34. The next step is to charge the brine and oil vessels 56 and 58 with an overhead pressure at about 30 psi, using $N_2$. At this juncture, the entire system has been purged of oxygen which materially alters the rate of corrosion. Through the use of process controller shown in FIG. 3, a particular temperature was selected and the temperature in the system was raised while circulating liquid through the test loop at about 2 feet per I 5 second. The valve 64 is used to assure added pressure to the loop until the loop was brought to a desired pressure level. Circulation was continued in an endless loop while the pressure was brought to the specified level. Then through the use of the controller shown in FIG. 3, the desired flow rate was selected. This involves operation of the pump 12. Then a base line data was obtained.

It is desirable to measure the corrosion rate until some equilibrium is reached. While no specific interval is mandated for this, it typically takes several hours, perhaps as many as eighteen hours. After establishing a base line of data, the next step is to inject the requisite amount of corrosion inhibitor material into the system using the valves 32 and 34. This requires opening the valves 32 and 34 to permit the liquid circulating in the system to displace the requisite volume of inhibitor for an interval. After the inhibitor is introduced in the concentration required, the valves 32 and 34 are closed to isolate the inhibitor source from the flow loop. All the while, the pump 12 is operated continuously. Corrosion measurements are taken periodically over these time intervals after closing the valves 32 and 34. Corrosion measurements are typically taken for many hours after closing the two valves just mentioned. Finally, after an adequate interval of testing, it is appropriate to turn off the system and discharge the pump 12 through the drain valve 32. This requires opening and closing other valves to assure discharge to some sort of waste container. Thereafter, purging of the loop is appropriate such as introducing an adequate volume of a solvent such as xylene which is circulated from perhaps one hour and then discharged to a container. After the xylene rinse, the next rinse can be obtained using isopropyl alcohol. Another rinse step of about one hour is often obtained by using tap water heated to 150° F. Finally, the loop is then purged with $CO_2$, and after assuring that the loop has been fully dried, all valves are closed and the loop can then be switched off.

In the foregoing procedure, a particular temperature for the circulating liquid is established. A system pressure is also established. The velocity of liquid in the loop can be controlled. To this end, the velocity is preferably set to the desired velocity through the test cells through use of flow control devices 26 and 28. As mentioned, it may be apt to use a flow velocity through one of the cells of one foot per second, ten feet per second in the second test cell and 50 feet in the third test cell. This provides three sets of data for a given solution.

As mentioned before in the specifics of one example, the foregoing test can be repeated using different concentration levels of the inhibitors. Examples were given where the concentration are 10, 50 and 100 ppm.

One advantage of the present system is that corrosion intensity can be observed with changes in velocity. It is suggested as a proposed theory that corrosion severity increases with an increase in shear and turbulence occurring in the flow line. This requires the use of great concentrations of the inhibitors to achieve comparable levels of protection. Moreover, the corrosion results can readily show irregularity or changes in relationship as a function of velocity. One aspect of corrosion inhibitor performance is related to the interaction of the inhibitor material with the face of the pipe. The corrosion process occurs in that region. It is particularly important to measure this in comparison with baseline measurements which are involved in system operation with a test fluid without any inhibitor. After some interval, the inhibitor can be added to shown the contrast or comparison between the baseline corrosion rate and the rate subject to the inhibitor protection. The corrosion rate is obtained by making measurements between the two coupons involved in the test system. This requires making measurements across the two coupons which are connected in a circuit for test purposes.

Typical conditions to be achieved during a test involve concentrations of corrosion inhibitors which approximate those that are necessary to achieve particular corrosion rates. Moreover, since this is sensitive to temperature, the corrosion test should be operated approximately at the temperature encountered in actual operation.

Among other things, the coupons require measurements before and after testing to determine weight loss. This requires that the coupons be weighed carefully to three or four decimal accuracy. At the time of use of coupons in the system, careful rinsing and purging of the test loop including the area of the test cell must be assured. It would seem appropriate to pressure test each of the test cells with inert gas where the test cell is elevated to perhaps 400 psi and discharged. This is done several time, at least 4 times to assure purging of oxygen from the test cell. The test cells are preferably separately purged with gas as noted above while installed in the loop by opening valves which communicate the test cells into the loop.

It is necessary after testing to remove the test coupons and make a visual inspection of them for pitting, blistering, surface discoloration and other visually determined damage. After a coupon has been used in a test, it is necessary to clean the coupon by acidizing with a suitable strong acid such as 15% HCl for perhaps one minute, scrubbing with a soap pad, rinsing with water and then rinsing with a mixture of 50% isopropanol and xylene. The coupons are then permitted to dry. After drying, the coupons are then weighed to determine the weight after testing. Needless to say, they are weighed before use. The corrosion weight rate is normally expressed in terms of mils per year or MPY. Sometimes a percentage factor is used. Such determinations are believed to be readily obtained through the use of the present apparatus.

One important added feature is a determination of the frequency responsive aspect of corrosion formation. That is, the corrosion which forms in the liquid flow path next to the wall and which systematically destroys a part of the wall is an ongoing problem. In one aspect of the present invention, the film is tested by making observations at the wall utilizing a variable frequency oscillator previously mentioned which is connected to a pair of terminals and hence across a pair of test coupons. This test procedure is particularly helpful as the frequency of the VFO is altered from one extreme to the other to cover the full range. So to speak, the corrosion which accumulates at the inner surface of the pipe which is in contact with and abutted against the liquid has a capacitive value. Loosely speaking, the thin film of corrosive material, measuring just a few angstroms in thickness, is particularly responsive to this kind of testing and data collection.

Certain aspects of corrosion as a function of flow velocity can then be obtained using this same liquid for the test loop. In one aspect, the liquid is circulated through the system so that the liquid interacts with the test coupons and forms the required signal to indicate the corrosion rate. Since three test cells are used and they are operated at different specific velocities, the corrosion rate should indicate any dependence of corrosion inhibition dependent on or related to velocity. Generally speaking, the velocity at which corrosion markedly increases is not a linear relationship; it is sometimes difficult to determine this relationship except by conducting numerous test of the sort set forth in this disclosure. The numerous test typically will require that the system be operated for a long interval of time so that proper date of measurements can be obtained.

While the foregoing is directed to the foregoing embodiment. The scope is determined by the claims which follow.

I claim:

1. An apparatus for testing corrosion of a flowing fluid, the apparatus comprising:
   a) a pump connected with a source of fluid having a specified formulation to simulate a flow situation wherein said pump delivers the flowing fluid at a specified pressure;
   b) a test cell serially connected with said pump so that the fluid delivered thereby is directed through the test cell and wherein the test cell includes at least one exposed test coupon in contact with the flowing fluid;
   c) a measuring circuit connected to said coupon for obtaining measurements relating to corrosion at said coupon;
   d) a flow controller to adjust the fluid flow velocity through the test cell; and
   e) a heat controller for controlling the temperature of the flowing fluid prior to flowing through the test cell.

2. The apparatus of claim 1 further including multiple test cells provided with fluid flow therethrough wherein at least one of said test cells is serially arranged with a separate flow controller for controlling the fluid velocity therethrough so that fluid flows at controlled velocities through said test cells.

3. The apparatus of claim 2 including at least two test cells exposed simultaneously to the fluid at two velocities.

4. The apparatus of claim 3 including an injector for adding a corrosion inhibitor to the flowing fluid.

5. The apparatus of claim i wherein the pump is connected to flow fluid in an endless loop, and the loop is pressurized to a selected minimum pressure thereby affecting the fluid flow velocity and pressure within the endless loop.

6. The apparatus of claim 5 including a pressurized gas source and pressure regulator connected thereto and wherein the pump raises fluid pressure to a pressure above the selected minimum pressure thereby further affecting pressure within the endless loop.

7. The apparatus of claim 1 wherein said test cell is serially connected with said pump and arranged to return line providing for endless circular flow thereof, and further wherein said endless flow is provided by the pump for an interval of several hours; and also including a gas supply for adding an inert gas to said loop to thereby control pressure in said loop to a specified pressure level independent of operational parameters of said pump.

8. The apparatus of claim 7 including a second test cell connected in a parallel return line of said loop exposed Simultaneously to a second fluid flow velocity controlled by a second flow controller.

9. The apparatus of claim 7 including three parallel return lines wherein a test cell is connected in each of the return lines.

10. The apparatus of claim 9 wherein a flow controller in each parallel return line provides different fluid flow velocities simultaneously to said test cells.

11. A method of testing rate of corrosion of a flowing fluid which is corrosive wherein the method comprises the steps of:
   a) forming a fluid mixture corresponding to a fluid to be tested for corrosion interaction;
   b) delivering the fluid under pressure and at a controlled temperature so that the fluid flows in an endless loop and is recirculated in the endless loop for a requisite interval;
   c) positioning a test cell in the loop wherein the test cell has at least two electrodes and one electrode is a sacrificial test coupon formed of a specified test material and is exposed to the fluid flowing therein and making measurements across said test coupon to obtain data indicative of the rate of coupon corrosion; and
   d) measuring the rate of loss of the coupon over a period of time in a specified test procedure.

12. The method of claim 11 wherein data is obtained for a specified pressure, temperature and velocity, and including the step of adding an inhibitor to the flowing fluid and obtaining data thereafter.

13. The method of claim 12 including the step of positioning a flow controller serially with a test cell so that velocity is varied to a desired range.

14. The method of claim 13 including the steps of obtaining corrosion data for different velocities simultaneously.

15. The method of claim 14 including the step of obtaining corrosion data for different pressures or temperatures.

16. A test cell for use in corrosion test system comprising:
   a) a test cell having an inlet and spaced outlet;
   b) a test fluid flow system connected to said inlet and said outlet so that fluid is circulated over a period of time through said test cell at a selected pressure, temperature, and velocity prior flowing through said test cell, Wherein said pressure, temperature and velocity can be varied;
   c) an internal passage through said test cell for the flowing fluid;
   d) a sacrificial metal surface comprising a portion of the side wall of said passage;
   e) an electrical insulative sleeve isolating said metal surface;
   a test circuit connecting with said metal surface.

17. The test cell of claim 16 including a second surface isolated from the first metal surface in said metal test cells.

* * * * *